United States Patent [19]
Sramek

[11] Patent Number: 4,836,214
[45] Date of Patent: Jun. 6, 1989

[54] ESOPHAGEAL ELECTRODE ARRAY FOR ELECTRICAL BIOIMPEDANCE MEASUREMENT

[75] Inventor: Bohumir Sramek, Irvine, Calif.
[73] Assignee: Bomed Medical Manufacturing, Ltd., Irvine, Calif.
[21] Appl. No.: 936,324
[22] Filed: Dec. 1, 1986
[51] Int. Cl.⁴ .............................................. A61B 5/02
[52] U.S. Cl. .................................. 128/693; 128/713; 128/734
[58] Field of Search .............. 128/642, 693, 734, 780, 128/784, 786, 713, 691–692

[56] References Cited

U.S. PATENT DOCUMENTS

| | | | |
|---|---|---|---|
| Re. 30,101 | 9/1979 | Kubicek et al. | 128/734 X |
| Re. 31,377 | 9/1983 | Mylrea et al. | 128/642 |
| 2,949,910 | 8/1960 | Brown et al. | 128/2.05 |
| 3,480,003 | 11/1969 | Crites | 128/734 X |
| 3,499,435 | 3/1970 | Rockwell et al. | 128/2.05 |
| 3,734,094 | 5/1973 | Calinog | 128/2.06 |
| 3,742,936 | 7/1973 | Blanie et al. | 128/713 |
| 3,884,219 | 5/1975 | Richardson et al. | 128/2 R |
| 3,951,136 | 4/1976 | Wall | 128/2.06 |
| 3,957,037 | 5/1976 | Fletcher et al. | 128/693 X |
| 4,176,660 | 12/1979 | Mylrea et al. | 128/671 |
| 4,304,239 | 12/1981 | Perlin | 128/642 |
| 4,304,240 | 12/1981 | Perlin | 128/671 |
| 4,314,095 | 2/1982 | Moore et al. | 128/642 X |
| 4,349,031 | 9/1982 | Perlin | 128/642 |
| 4,369,794 | 1/1983 | Furler | 128/671 |
| 4,380,237 | 4/1983 | Newbower | 128/734 X |
| 4,444,195 | 4/1984 | Gold | 128/786 X |
| 4,450,527 | 5/1984 | Sramek | 128/693 X |
| 4,475,555 | 10/1984 | Linder | 128/670 |
| 4,476,872 | 10/1984 | Perlin | 128/642 |
| 4,611,604 | 9/1986 | Botvidsson et al. | 128/784 |
| 4,674,518 | 6/1987 | Salo | 128/734 X |

Primary Examiner—Kyle L. Howell
Assistant Examiner—Angela D. Sykes
Attorney, Agent, or Firm—Knobbe, Martens, Olson & Bear

[57] ABSTRACT

An array of electrical bioimpedance electrodes are provided on a hollow, flexible tube that is insertable into the esophagus of a patient. Four electrodes are positioned on the outer wall of the tube. Four wires are run through the hollow center portion of the tube and are connected through the wall of the tube to a respective one of the four electrodes. The four wires are connectable to an electrical bioimpedance measurement device. Two of the electrodes are connected to a high frequency, low magnitude constant current source so that a current can be injected into the thorax of the patient between the two electrodes. The other two electrodes are connected to the sensing input of the electrical bioimpedance measurement device and detect a voltage induced in the thorax of the patient that varies in accordance with the electrical bioimpedance changes in the patient. The tube is positioned in the esophagus proximate to the descending thoracic aorta so that the primary source of electrical bioimpedance changes is the flow of blood in the descending thoracic aorta. The present invention is used to determine the cardiac output of the patient that results in the flow of blood in the descending thoracic aorta.

10 Claims, 2 Drawing Sheets

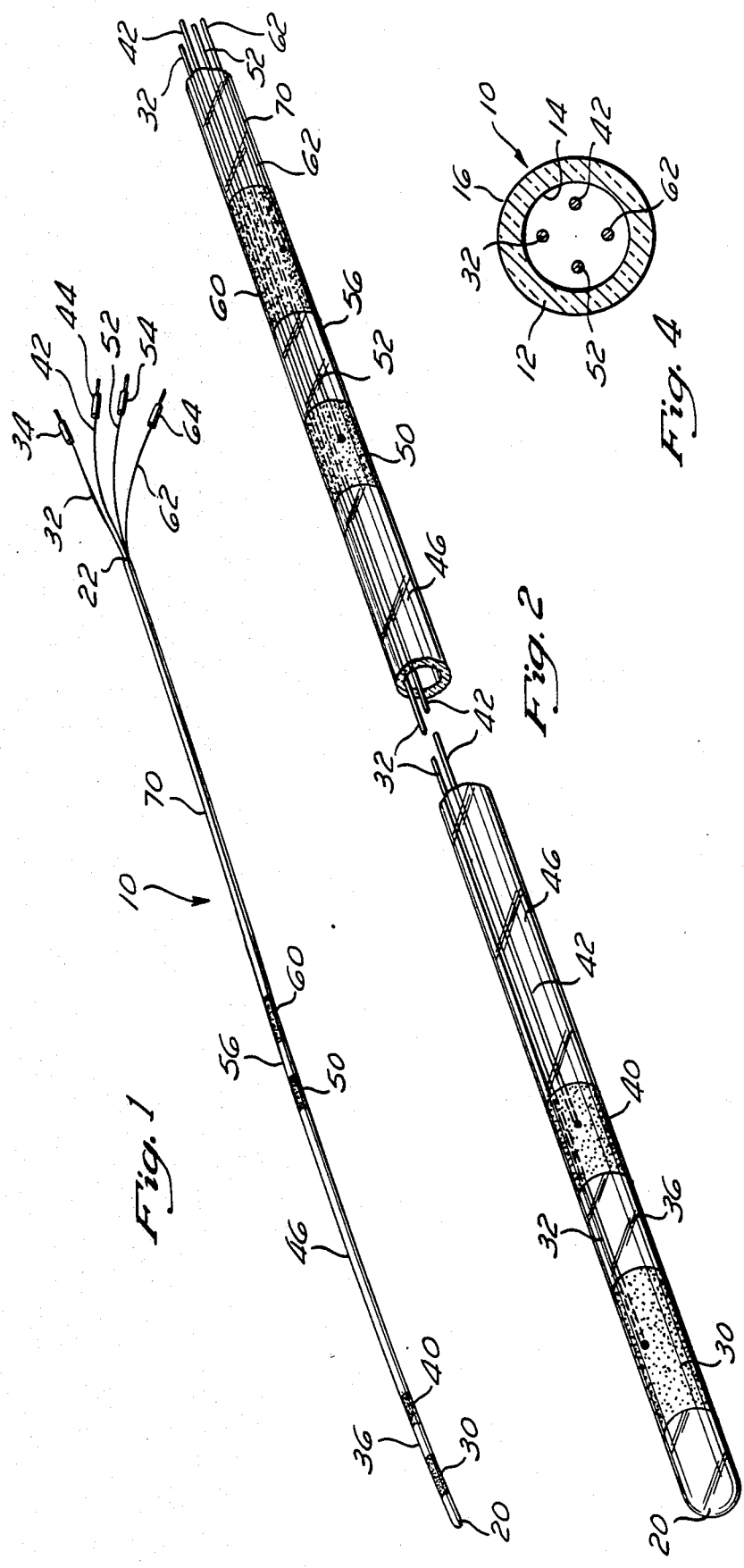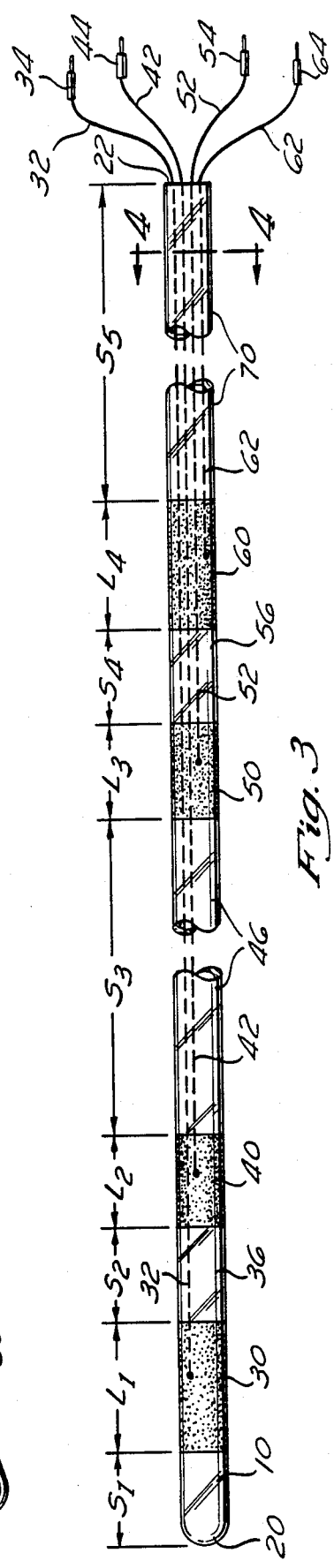

1

ESOPHAGEAL ELECTRODE ARRAY FOR ELECTRICAL BIOIMPEDANCE MEASUREMENT

BACKGROUND OF THE INVENTION

1. Field of the Invention

This invention is generally related to an apparatus for measuring parameters associated with the flow of blood through a body segment. More particularly, this invention is related to an apparatus for monitoring the cardiac output by measuring blood flow in the thorax of the body of a human or an animal.

2. Description of the Related Art

Cardiac output is the volume of blood which the heart pumps in one minute and is one of the most important cardiovascular parameters. The cardiac output reflects the supply of oxygen and nutrients to tissue. Measurements of cardiac output provide invaluable clinical information for quantifying the extent of cardiac dysfunction, and for monitoring the operation of the heart during exercise, surgery, or the like.

Cardiac output may be measured either invasively or noninvasively. The invasive techniques for measuring cardiac output involve penetration of the skin by a catheter, require complex instrumentation which must be operated by skilled personnel, and present a risk to the patient. Invasive techniques such as indicator dilution and thermal dilution allow only intermittent measurement of cardiac output since it is possible to obtain only one determination of cardiac output per injection in dilution methods.

Noninvasive techniques for measuring cardiac parameters include ballistocardiography, electrical bioimpedance measurements, ultrasonics, phonocardiography, and vibrocardiography. The present invention is concerned primarily with the use of electrical bioimpedance measurements. Electrical bioimpedance measurements permit quantification of blood flow as a result of changes in electrical conductivity of a body segment. The electrical impedance technique for measuring cardiac output is based upon changes in thoracic electrical impedance caused by cardiovascular activity. A full and complete discussion of electrical bioimpedance measurements and instrumentation for performing the measurements is set forth in commonly assigned U.S. Pat. No. 4,450,527, issued on May 22, 1984, the disclosure of which is incorporated herein by reference.

As set forth in U.S. Pat. No. 4,450,527, electrical bioimpedance measurements are obtained by injecting a high frequency, low magnitude constant current through a segment of a patient's body by positioning a first current injecting electrode at one boundary of the body segment and a second current injecting electrode at a second boundary of the body segment. Of course, as set forth in U.S. Pat. No. 4,450,527, multiple electrodes may be advantageously used for each of the current injecting electrodes. Changes in the electrical bioimpedance of the body caused by blood flow in the defined body segment are detected by measuring a voltage developed across the body segment. This voltage is measured by a set of voltage sensing electrodes which are positioned on the body segment within the boundaries defined by the current injecting electrodes. Again, multiple electrodes can be used for each of the voltage sensing electrodes.

Typically, the body segment chosen for determining cardiac output is the thorax of the patient. Thus, as illustrated in U.S. Pat. No. 4,450,527, in an exemplary measurement procedure, a pair of upper sensing electrodes are attached to the patient's neck on opposite sides at the intersections of a line encircling the root of the neck with the frontal plane of the patient. A pair of upper current injectng electrodes are attached to the patient's neck approximately five centimeters above the upper sensing electrodes. A pair of lower thoracic anterior sensing electrodes are placed at the intercostal space at each midclavicular line at the xiphoid process level. A pair of posterior sensing electrodse are placed at the same level as the anterior sensing electrodes at the intercostal space at the midscapular line. A first pair of lower current injecting electrodes are located approximately five centimeters below the lower thoracic anterior sensing electrodes. A second pair of lower injecting electrodes are attached to the patient, approximately five centimeters below the posterior sensing electrodes. Typically, the electrodes are spot electrodes which are pregelled and are attached to the prepared skin of the patient.

The electrodes are electrodes connected by wires to a bioimpedance measurement apparatus, such as the apparatus described in U.S. Pat. No. 4,450,527. Other measurement devices, having varying degrees of sophistication and cost could also be used. For the purposes of this application, reference will be made to the apparatus described in U.S. Pat. No. 4,450,527.

As set forth in U.S. Pat. No. 4,450,527, the changes in the electrical bioimpedance of the patient can be continuously measured during exercise or other diagnostic activity to thereby determine the cardiac output of the patient. Several cardiovascular variables can be measured and displayed using the measurement device.

As one can envision, or readily observe by reviewing U.S. Pat. No. 4,450,527, a number of electrical interconnection wires and corresponding electrodes are required to make the thoracic electrical bioimpedance measurements. Thus, although the device described in U.S. Pat. No. 4,450,4527, and other such devices have substantial diagnostic uses, the use of electrodes applied to the skin and wires emanating from the electrodes may present significant problems if bioimpedance measurements are desired during thoracic surgery or upper abdominal surgery. During such surgery, when the patient is sterile and draped with surgical cloths, it is sometimes difficult to verify the correct and reliable connection of the surface electrodes. During the thoracic surgery, the metal retractors, used to hold the rib cage open, may alter the electrical field distribution and interfere with the accuracy of the data obtained by electrical bioimpedance measurements. Similarly, if a patient is in septic shock, wherein the thoracic wall is highly perfused with liquid, the increased conductivity of the superficial layers of the thoracic wall will affect the absolute value of the stroke volume data and may therefore prevent the maseurement of useful data. The primary source of impedance variation originates in the descending thoracic aorta; however, the effects of the changes in volume of the thoracic aorta are less pronounced while using surface electrodes because the variation of electrical bioimpedance of all other thoracic sources, such as the volume of the blood in the heart and in the pulmonary circulation, will get superimposed over the thoracic aorta bioimpedance variation, thus diminishing the resolution of the measurement. Therefore, a need exists for an apparatus for measuring thoracic bioimpedance changes that are more responsive to the volume of the blood in the thoracic aorta and which can be used during surgical procedures without interfering with the procedure and without being substantially affected by metal instruments used during the procedure.

SUMMARY OF THE INVENTION

The present invention redues or eliminates the problems associated with the skin-mounted electrode arrays discussed above by providing an electrode array that is insertable into the esophagus of a patient. The electrode array includes a flexible tube having a first end and a second end, and having an outside surface. The outside surface gas an outside diameter that is selected so that the flexible tube is easily insertable into the esophagus of the patient. The electrode array includes at least first, second, third and fourth electrodes that are disposed on the outside surface of the flexible tube. Each of the electrodes has an outer surface which has an outside diameter that is selected to make contact with the inside surface of the esophagus. The electrodes are positioned on the outside surface of the tube so that the second electrode and the third electrode are disposed between the first electrode and the fourth electrode. The electrode array further includes first, second, third and fourth wires that are electrically connected to the first, second, third and fourth electrodes, respectively. The wires extend from the respective electrodes and out the second end of the flexible tube.

The first wire and the fourth wire of the electrode array are connectable to a source of high frequency, low magnitude constant current so that the high frequency constant current is injectable into the body of the patient between the first and fourth electrodes. The second and third wires are connectable to the input of a voltage detection circuit so that a voltage developed in the body of the patient in response to the high frequency constant current is conducted from the second and third electrodes to the voltage detection circuit.

In preferred embodiments of the present invention, the four electrodes are constructed from silver-plated stainless steel. Also preferably, the stainless steel is formed as a mesh so as to maintain the flexiblity of the tube.

Preferably, the flexible tube has a hollow inner portion so that the four wires passing from the four electrodes to the second end of the tube pass through the hollow portion. In preferred embodiments of the invention, the first electrode and the fourth electrode are spaced apart by a distance that is selected to be greater than the distance between the diaphragm of the patient and the top of the aortic arch of the patient. The second and third electrode are disposed between the first and fourth electrode and are spaced apart such that the distance between the second electrode and the third electrode is less than the distance between the bottom of the aortic arch of the patient and the top of the diaphragm of the patient.

The present invention also includes a method of using an array of four electrodes disposed on the outer surface of a flexible tube. The method includes the steps of inserting the flexible tube into the esophagus of a patient to a position so that a first electrode is positioned below the diaphragm of the patient and a second electrode is positioned above the diaphragm of the patient. A third electrode is positioned below the aortic arch of the patient and a fourth electrode is positioned above the aortic arch of the patient. A high frequency constant current is applied to the first and fourth electrodes so that the current passes through the thorax of the patient between the first and fourth electrodes. A voltage is developed in the thorax of the patient and is conducted from the second and third electrodes to detection circuitry. The voltage so developed is responsive to the electrical bioimpedance changes in the body during each cardiac cycle. The voltage is differentiated and provided as an output signal having a magnitude that is proportional to the rate of change in the electrical bioimpedance of the body. The rate of change is monitored as the electrode array is positioned in the espohagus. The electrode array is positioned so that the magnitude of the output signal is at a selected magnitude between a maximum detected magnitude and a minimum detected magnitude. Thereafter, the electrode array provides a means for monitoring the cardiac output without requiring an external electrode array.

BRIEF DESCRIPTION OF THE DRAWINGS

FIG. 1 is a perspective view of the esophageal electrode array of the present invention, showing the flexible tube, four electrodes disposed on the flexible tube, and interconnection wires for providing electrical connection to the electrodes.

FIG. 2 is an enlarged prespective view of the esophageal electrode array of FIG. 1, having a portion of the flexible tube broken away to show the first and second interconnection wires disposed in the hollow inner portion of the tube.

FIG. 3 is an elevation view of the esophageal electrode array of FIG.1 and 2.

FIG. 4 is a cross-sectional view of the flexible tube of FIG. 1, 2, and 3 taken along the lines 4—4 in FIG. 3.

DETAILED DESCRIPTION OF THE PREFERRED EMBODIMENT

A preferred embodiment of the esophageal electrode array of the present invention is illustrated in FIGS. 1–4. The esophageal electrode array includes a nonconductive hollow tube 10, having sufficient rigidity that it will not kink during the introduction of the tube into the esophagus of a patient, and having sufficient flexibility to allow introduction into the esophagus via the nose or mouth. In exemplary embodiments, the tube 10 is constructed from PVC or another sterilizable plastic material.

As shown in FIG. 4, the tube 10 has a hollow inner cavity defined by wall 12 having an inner surface 14 on outer surface 16. The inside diameter, as defined by the inner surface 14, is approximately $\frac{1}{4}$-inch in an exemplary embodiment intended for adult use. The outside diameter of the tube 10, as defined by the outer surface 16 is approximately $\frac{3}{8}$-inch in the same exemplary embodiment, thus providing a wall thickness of approximately 1/16-inch. The diameter of the tube 10 has to be compatible with the introductory passage through the nose or the throat and gave dimensions compatible with the diameter of the esophagus. The outer diameter of the tube 10 is sufficiently large so that the outer surface 16 makes contact with the inner wall of the esophagus, yet the outer diameter is sufficiently small to enable the tube 10 to be inserted into the espohagus of a patient without requiring excessive force. The foregoing dimensions are exmplary for a typical adult and can be varied to accommodate large and small esophaguses.

Figure 5:
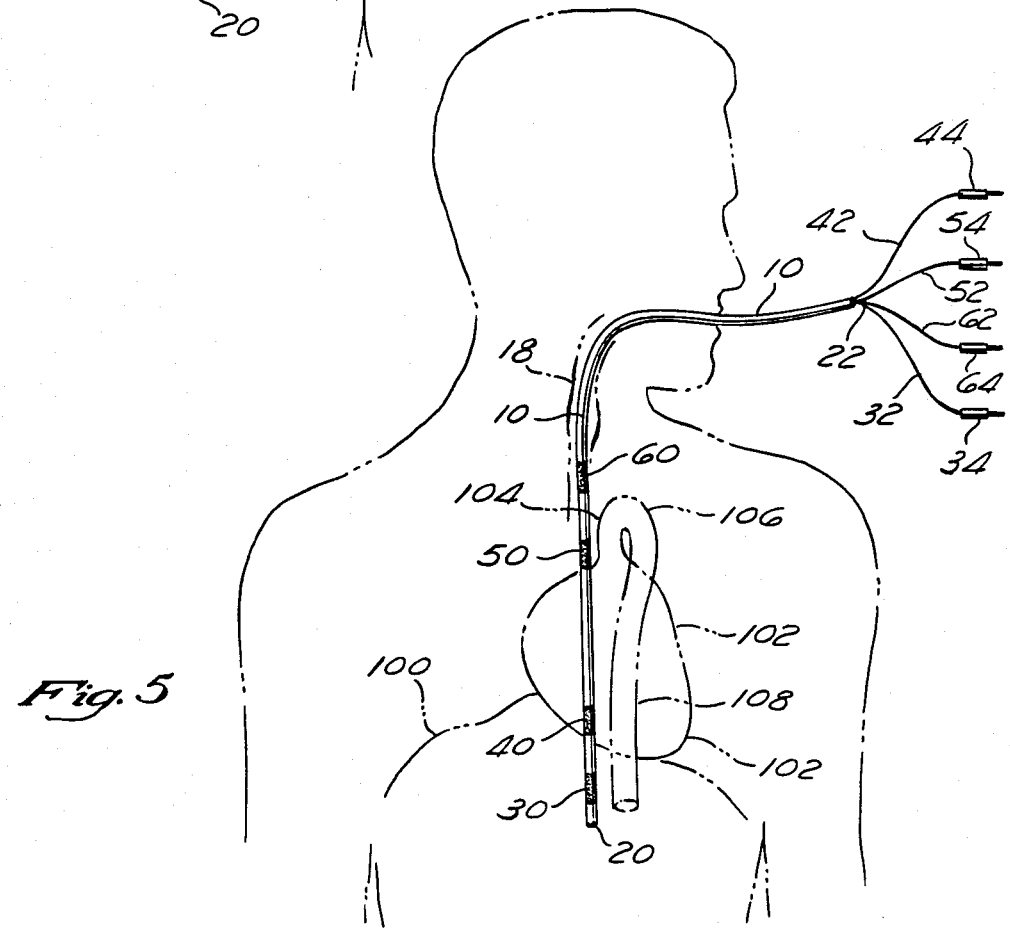
FIG. 5 illustrates the esophageal electrode array of FIG. 1 inserted through the patient's mouth and positioned in the esophagus proximate to the descending thoracic aorta.

The tube 10 has a length that is selected to provide sufficient length to insert the tube 10 through the mouth or nose and then into the esophagus 18 of a patient, as illustrated in FIG. 5. Preferably the tube 10 is insertable into the esophahus 18 to a sufficent depth that a first end 20 of the tube 10 extends below the diaphragm of the patient when the diaphragm is in its highest position (i.e., during exhalation). A second end 22 of the tube 10 extends out of the mouth or nose of the patient for a distance sufficient to permit easy handling of the second end by medical personnel. In one preferred embodiment, the tube 10 has a total length of 66 The first end 20 of the tube 10 is preferably bullet-shaped so that tube 10 can be easily inserted into the esophagus of the patient, and is preferably closed to prevent mucous or other contents of the esophagus or the stomach from entering into hollow inner portion of the tube 10.

The tube 10 has four electrodes disposed on the outer surface. A first electrode 30 is located proximate to the first end 20. For example, the electrode 30 may be located at a distance of approximately two centimeters from the first end 20, as illustrated by the distance $S_1$ in FIG. 3. The electrode 30 is constructed from a non-corrosive, low impedance conductive material so as to provide good electrical contact with the inside wall of the esophagus when the tube 10 is inserted into the esophagus, as illustrated in FIG. 5. For example, in one embodiment of the present invention, the electrode 30 is constructed of stainless steel that is attached to the tube 10 without significant disruption of the smoothness of the surface of the tube. The electrode can be a stainless steel ring, or, in a particularly preferred embodiment, is a stainless steel mesh to thereby maintain the flexibility of the tube 10. In alternative embodiments, the electrode 30 can be formed by impregnating the plastic wall 12 of the tube 10 with a conductive material in a defined area.

The first electrode 30 is electrically connected to a first wire 32 whcih passes through the wall 12 into the hollow inner portion of the tubing 10. The wire 32 is sufficiently long so that it extends from the first electrode 30, through the hollow portion of the tube 10, to the second end 22, wherein a portion of the first wire 32 extends from the second end 22. The end of first wire 32 extending from the second end 22 of the tube 10 is preferably terminated with a first connector 34, such as an 80-mil electrocardiograph-type pin. The connector 34 is connectable to an electrical bioimpedance monitoring device such as the device described in U.S. Pat. No. 4,450,527. In one particular embodiment, the wire 32 is an insulated, 24 AWG copper wire.

The first electrode 30 has a length along the longitudinal axis of the tube 10 that is sufficient to provide substantial surface contact with the inner wall of the espohagus of the patient. For example, in an exemplary preferred embodiment, the first electrode 30 has a length, shown as $L_1$ in FIG. 3, of approximately 3 centimeters.

A second electrode 40 is spaced apart from the first electrode 30 by a portion 36 of the tube 10. The portion 36 has a length $S_2$, that is advantageously approximately 2 centimeters. The second electrode 40 is constructed in a manner similar to that of the construction of the first electrode 30. The second electrode 40 is utilized as a sensing electrode, and thus does not carry a substantial amount of current. In the exemplary preferred embodiment, described herein, the second electrode 40 has a longth $L_2$ of approximately 2 centimeters.

The second electrode 40 is electrically connected to a second wire 42 which passes through the wall 12 into the hollow inner portion of the tubing 10, and extends through the hollow inner portion of the tubing 10 to and out of the second end 22. The second wire 42 is substantially identical to first wire 32, and terminates in a second connector 44, which is advantageously an electrocardiograph-type pin, similar to the first connector 34. Preferably, the first connector 34 and the second connector 44 are color-coded so that the two connectors can be readily distinguished.

A third electrode 50 is spaced apart from the second electrode 40 by a portion 46 of the tube 10. The portion 46 has a length $S_3$, which, in the exemplary preferred embodiment described herein, is approximately 24 centimeters. The third electrode 50 is a sensing electrode and, as with the second electrode 40, has a length $L_3$ approximately 2 centimeters.

The third electrode 50 is connected to third wire 52, which extends through the hollow portion of the tube 10 and out the second end 22. The third wire 52 terminates in a third connector 54, which is also preferably an electrocardiograph-type pin. As with the other connectors, the third connector 54 is color-coded to distinguish it from the other connectors.

A fourth electrode 60 is spaced from the third electrode 50 by a portion 56 of the tube 10. The portion 56 has a length $S_4$, which is advantageously approximately 2 centimeters. The fourth electrode 60 is a current injecting electrode and advantageously has a length $L_4$ of approximately 3 centimeters.

The fourth electrode 60 is electrically connected to a fourth wire 62 which passes through the hollow portion of the tube 10 and out the second end 22. The fourth wire 62 termiates in a fourth plug 64 which is advantageusly an electrocardiograph-type pin that is color coded to distinguish it from the other three connectors.

The forth electrode 60 is spaced apart from the second end 22 by a portion 70 of the tube 10 that has a length $S_5$ that is advantageously approximately 30 centimeters.

The foregoing dimensions of the tube 10 and the electrodes 30, 40, 50, and 60 be readily varied in accordance with respective dimensions of the patient or other subject being monitored.

In preferred embodiments, the open second end 22 of the tube 10 is plugged with medical grade silicon rubber for a distance of approximately 2 centimeters to prevent the entry of any foreign material into the hollow inner portion of the tube 10. Referring now to FIG. 5, the operation of the present invention for providing measurements of electrical bioimpedance will be discussed. In FIG. 5, the tube 10 is shown inserted through the mouth of a patient and into the esophagus 118 (shown in phantom). The patient's diaphragm is pictorially illustrated by a phantom line 100. The tube 10 is inserted into the patient's body a sufficient distance so that the first electrode 30 is positioned below the diaphragm 100. A preferred method for positioning the first electrode 30 will be described more fully below. The patient's heart is pictorially represented by a phantom outline 102 above the diaphragm 100. The ascending portion of the aorta is represented by phantom lines 104, the aortic arch is represented by phantom lines 106, and the descending thoracic aorta is represented by phantom lines 108, As is well known, the esophagus 18 passes dorsal and to the right of the aortic arch 106, and descends in the posterior mediastinum along the right side of the descending thoracic aorta 108, then runs ventral and a little to the left of the thoracic aorta 108, and enters the abdomen through the diaphragm 100 at the level of the tenth thoracic vertebra. (See for example, Henry Gray, *Anatomy of the Human Body*, edited by Charles Mayo Goss, (29th American Edition, Lea & Febiger, 1973), page 1200.) Thus, when the tube 10 is in place in the esophagus 18, as illustrated in FIG. 5, it is proximate to the descending thoracic aorta 108.

The spacings between the first electrode 30, the second electrode 40, the third electrode 50, and the fourth electrode 60, are selected so that when the first electrode 30 is positioned below the diaphragm 100 of the patient when the diaphragm 100 is in its highest position (i.e., during exhalation), the second electrode 40 is positioned just above the diaphragm 100 proximate to the descending thoracic aorta 108. Similarly, the third electrode 50 is positioned proximate to the descending thoracic aorta 108, just below the thoracic aortic arch 106. The fourth electrode 60 is positioned above the aortic arch 106. Preferably, the lentgth of the tube 10 from the lowermost edge of the second electrode 40 to the uppermost edge of the third electrode 50 (i.e., the length represented by $L_2+S_3+L_3$), is less than the length of the descending thoracic aorta 108 from the aortic arch 106 to the top of the diaphragm 100, when the diaphragm 100 is at its highest position.

Figure 6:
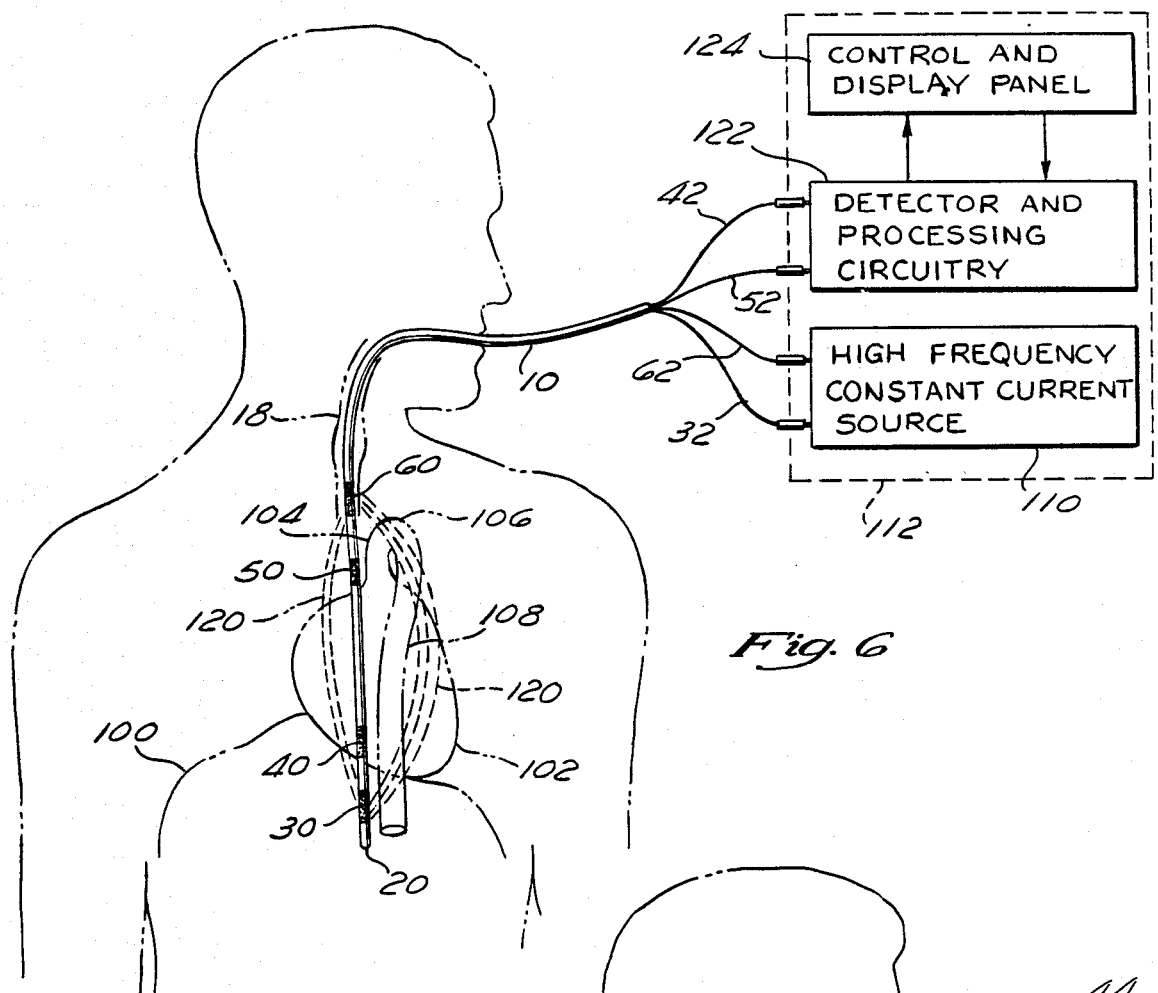
FIG. 6 illustrates the esophageal electrode array of FIG. 5 inserted in the esophagus and electrically connected to a cardiac output monitor, and further showing an exemplary electrical field pattern generated by the current injecting electrodes of the array.

In FIG. 6, the first wire 32 and the fourth wire 62 are shown connected to a high frequency, low magnitude constant current source, such as a current source 110 in a bioimpedance monitoring device 112. The bioimpedance monitoring device 112 is advantageously a device such as described in U.S. Pat. No. 4,450, 527. The current from the current source 110 causes a spindle-shaped electric field to develop between the first electrode 30 and the fourth electrode 60 and envelop the descending aorta 108. The spindle-shaped electric field is represented by phantom lines 120 in FIG. 6. As illustrated, the spindle-shaped electric field 120 is concentrated around the descending thoracic aorta 108 because the large amount of blood in the descending thoracic aorta 108 provides a relatively substantial amount of conductivity compared to the surrounding tissues.

The spindle-shaped electric field 120 induces a high frequency voltage in the descending thoracic aorta 108 that is proportional to the electrical bioimpedance of the descending aorta 108 and the constant current flowing therein. The second electrode 40 and the third electrode 50 are positioned in the esophagus 18, proximate to the descending thoracic aorta 108. Thus, the second electrode 40 and the third electrode 50 receive a voltage induced by the high frequency current flowing from the first electrode 30 to the fourth electrode 60. This induced voltage is conducted from the second electrode 40 and the third electrode 50 via the second wire 42 and the third wire 52 to detctor and processing circuitry 122 located within the bioimpedance monitoring device 112. The detector and processing circuitry 122 provides information to a control and display unit 124 that functions in the manner described in U.S. Pat. No. 4,450,527.

For example, the detector and processing circuitry 122 provides signals to the control and display unit 124 that represent cardiac parameters such as stroke volume, cardiac output, and dZ/dt (i.e., change in electrical bioimpedance per unit time).

Since the second electrode 40 and third electrode 50 are located in the esophagus proximate to the descending thoracic aorta 108, the voltage devloped between the second electrode 40 and the third electrode 50 will be primarily determined by the blood flow in the descending thoracic aorta 108, and will be less affected by blood flow in the heart, the pulmonary arteries, and the like. Thus, the location of the present invention is particularly advantageous in increasing the accuracy of the measurements obtained through the bioimpedance technique. Furthermore, since the second electrode 40 is positioned above the diaphragm 100 at the highest position of the diaphragm 100, the movement of the diaphragm 100 during respiration does not substantially affect the accuracy of the measurements.

As set forth in U.S. Pat. No. 4,450,527, the bioimpedance measuring apparatus determines the cardiac output by measuring the maximum positive value of the rate of change of the electrical bioimpedance with respect to time (i.e., dZ/dt). This maximum measurement is available as an output display on the control and display unit 124 of the bioimpedance measuring device 112. The measurement will remain substantially at its maximum value so long as the second electrode 40 is above the highest position of the diaphragm 100 and the third electrode 50 is below the aortic arch 106. Since the length of the tube 10 between the bottom of the second electrode 40 and the top of the third electrode 50 is preferably selected to be less than the length of the descending thoracic aorta 108, the measurement will remain substantially at the maximum value for a range of positions for the second electrode 40 and the third electrode 50. This feature is utilized to position the esophageal electrode array of the present invention by inserting the tube 10 so that the electrodes 30, 40, 50 and 60 are approximately in the desired positions in the esophagus of the patient. The magnitude of dZ/dt is displayed on the control and display unit 124, and the magnitude is monitored by the person inserting the tube 10. The tube 10 is then moved to obtain the boundary positions (i.e., the uppermost and lowermost positions) wherein the dZ/dt reading changes to and from the maximum value. Thereafter, the tube 10 is moved to a central position approximately halfway between the two boundary positions. Thus, in this central position, the tube 10 is located so that the second electrode 40 and the third electrode 50 are positioned between the diaphragm 100 and the aortic arch 106, alongside the descending aorta 108. Thereafter, the cardiac output can be monitored in a conventional manner during a surgical procedure, or other diagtnostic therapeutic procedure. By locating the third electrode 30 and the fourth electrode 50 in this manner, a small amount of movement of the esophageal electrode array within the esophagus 18 can be tolerated without causing a significant change in the accuracy of the measurements.

The esophageal array of the present invention can also advantageously be used as an electrocardiograph array by connecting the ground lead of an electrocardiograph measuring device to either the first electrode 30 or the fourth electrode 60, via the first wire 32 or the fourth wire 62 respectively, The ECG sensor inputs are connected to the second electrode 40 and the third electrode 50 via the second wire 42 and the third wire 52, respectively.

The present invention can be also used as an esophageal stethoscope by fabricating a stethoscope in the hollow inner portion of the tube 10, preferably in the portion 46 between the second electrode 40 and the third electrode 50.

Although the invention has been described above with reference to a specific preferred embodiment, modifications within the scope of the invention may be apparent to those skilled in the art. Therefore, the true scope of the invention is understood to be determined by the intended claims.

I claim:

1. An electrode array for determining the cardiac output of a patient, said electrode array being insertable into the esophagus of the patient so that bioimpedance measurements relating to cardiac output can be made when said electrode array is inserted into the esophagus of a patient, said electrode array comprising:
   a flexible tube having a first end and second end, and having an outside surface, said outside surface having an outside diameter selected so that said flexible tube is easily insertable into esophagus of a patient;
   at least first, second, third and fourth circumferential electrodes positioned on said outside surface of said tube and spaced apart from each other along the length of said tube, each said electrode having an outer surface, each said outer surface having an outside diameter at least as large as large as the inside diameter of said esophagus;
   said second electrode and said third electrode positioned along the length of said flexible tube between said first electrode and said fourth electrode, said second electrode separated from said third electrode by a distance of at least a multiple of said outside diameter of said tube; and
   first, second, third, and fourth wires connected to said first, second, third and fourth electrodes, respectively, said wires extending out of said second end of said flexible tube.

2. The electrode array as defined in claim 1, wherein said first wire and said fourth wire are connectable to a source of high frequency constant current so that said high frequency constant current is injectable into the body of said patient between said first and fourth electrodes, and said second and third wires are connectable to the input of a voltage detection circuit so that a voltage developed in said body in response to said high frequency constant current is conducted from said second and third electrodes to said voltage detection circuit.

3. The electrode array as defined in claim 1, wherein said first, second, third and fourth electrodes comprise stainless steel.

4. The electrode array as defined in claim 3, wherein said stainless steel of said first, second, third and fourth electrodes is formed as a mesh.

5. The electrode array as defined in claim 1, whereihn said tube has a hollow inner portion, and wherein said first, second, third and fourth wires pass through said hollow inner portion from said first, second, third and fourth electrodes, respectively, to and out of said second end of said tube.

6. An electrode array as defined in claim 1 wherein said outer surface of said flexible tube has substantially the same diameter as said outer surfaces of said electrodes.

7. An electrode array for determining the cardiac output of a patient, said electrode array being insertable into the esophagus of the patient so that bioimpedance measurement relating to cardiac output can be made when said electrode array is inserted into the esophagus of a patient, said electrode array comprising:
   a flexible tube having a first end and a second end, and having an outside surface, said outside surface having an outside diameter selected so that said flexible tube is easily insertable into the esophagus of a patient;
   at least first, second, third, and fourth circumferential electrodes positioned on said outside surface of said tube and spaced apart from each other along the length of said tube, each said electrode having an outer surface, each said outer surface having an outside diameter of approximately three-eighths of an inch to ensure contact with the inside surface of said esophagus;
   said second electrode and said third electrode positioned along the length of said flexible tube between said first electrode and said fourth electrode, said second electrode separated from said third electrode by a distance of at least a multiple of said outside diameter of said tube; and
   first, second, third, and fourth wires connected to said first, second, third and fourth electrodes, respectively, said wires extending out of said second end of said flexible tube.

8. An electrode array for determining the cardiac output of a patient, said electrode array being insertable into the esophagus of the patient so that bioimpedance measurements relating to cardiac output can be made when said electrode array is inserted into the esophagus of a patient, said electrode array comprising:
   a flexible tube having a first end and a second end, and having an outside surface, said outside surface having an outside diameter selected so that said flexible tube is easily insertable into the esophagus of a patient;
   at least first, second, third and fourth, circumferential electrodes positioned on said outside surface of said tube and spaced apart from each other along the length of said tube, each said electrode having an outer surface, each said outer surface having an outside diameter selected to ensure contact with the inside surface of said esophagus:
   said second electrode and said third electrode positioned along the length of said flexible tube between said first electrode and said fourth electrode, said second electrode separated from said third electrode by a distance of at least a multiple of said outside diameter of said tube, wherein:
   said first electrode and said fourth electrode are spaced apart by a distance selected to be greater than the distance between the diaphragm of said patient and the top of the aortic arch of said patient; and,
   said second electrode and said third electrode are spaced apart such that the distance between said electrode and said third electrode is less than the distance between the bottom of the aortic arch of the patient and the diaphragm of the patient; and
   first, second, third, and fourth wires connected to said first, second, third and fourth electrodes, respectively, said wires extending out of said second end of said flexible tube.

9. An electrode array for determining the cardiac output of a patient, said electrode array being insertable into the esophagus of a patient, said electrode array comprising:
- a flexible tube having a first end and a second end, and having an outside surface, said outside surface having an outside diameter selected so that said flexible tube is easily insertable into the esophagus of a patient and so that said outer surface makes substantial contact with the inner surface of said esophagus;
- at least first, second, third and fourth electrodes disposed on said outside surface, wherein:
- each said electrode has an outer surface, each said outer surface having an outside diameter selected to make contact with the inside surface of said esophagus;
- said first electrode and said fourth electrode are spaced apart by a distance selected to be greater than the distance between the diaphragm of said patient and the top of the aortic arch of said patient; and
- said second elcetrode and said third electrode are disposed between said first electrode and said fourth electrode and are spaced apart such that the distance between said second electrode and said third electrode is less than the distance between the bottom of the aortic arch of the patient and the diaphragm of the patient; and
- first, second, third, and fourth wires electrically connected to said first, second, third, and fourth electrodes, respectively, said wires extending out of said second end of said flexible tube.

10. A method of measuring the cardiac output of a patient by the insertion of an electrode array into the esophagus of a patient, comprising the step of:
- inserting a flexible tube into the esophagus of a patient, said flexible tube having first, second, third and fourth electrodes on the surface thereof;
- positioning said first electrode below the highest position of the diaphragm of the patient;
- positioning said second electrode above the highest position of the diaphragm of the patient, spaced apart from said first electrode;
- positioning said third electrode below the aortic arch of said patient, spaced apart from said second electrode;
- positioning said fourth elecrode above the aortic arch spaced apart from said third electrode;
- applying a high frequency constant current to said first and fourth electrodes so that said current flows through the tissues of said patient between said first and fourth electrodes; and
- detecting a voltage developed across said second and third electrodes caused by said current flowing in said tissues of said patient, said voltage varying in accordance with changes in the electrical bi-oimpedance of said tissues.

* * * * *